March 16, 1965 D. L. ARMSTRONG ETAL Plant Pat. 2,488
ROSE PLANT
Filed Jan. 16, 1964 2 Sheets-Sheet 1
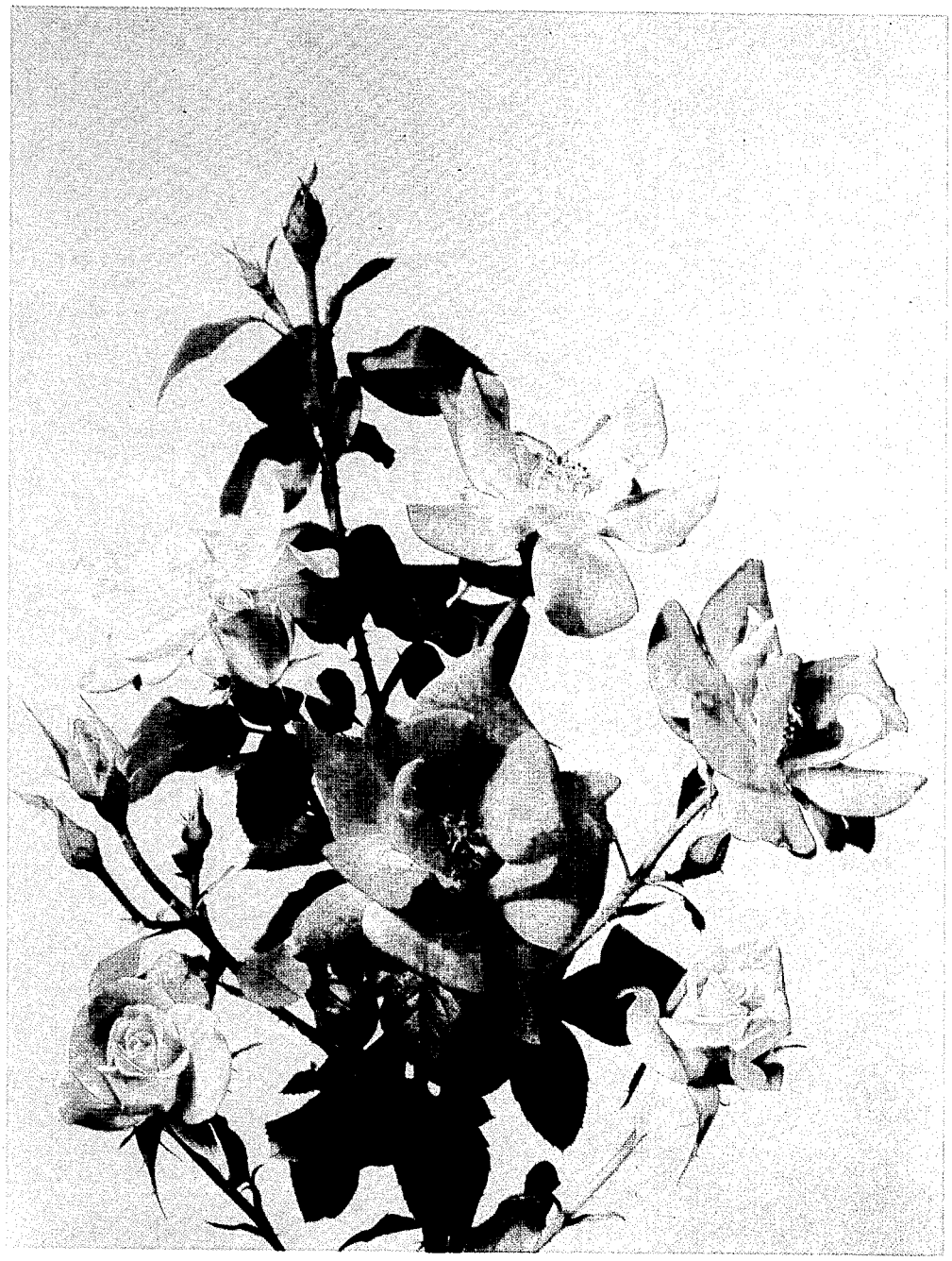
Inventors.
D. L. Armstrong and
H. C. Swim
By: Robb & Robb
Attorneys.

March 16, 1965 D. L. ARMSTRONG ETAL Plant Pat. 2,488
ROSE PLANT
Filed Jan. 16. 1964 2 Sheets-Sheet 2
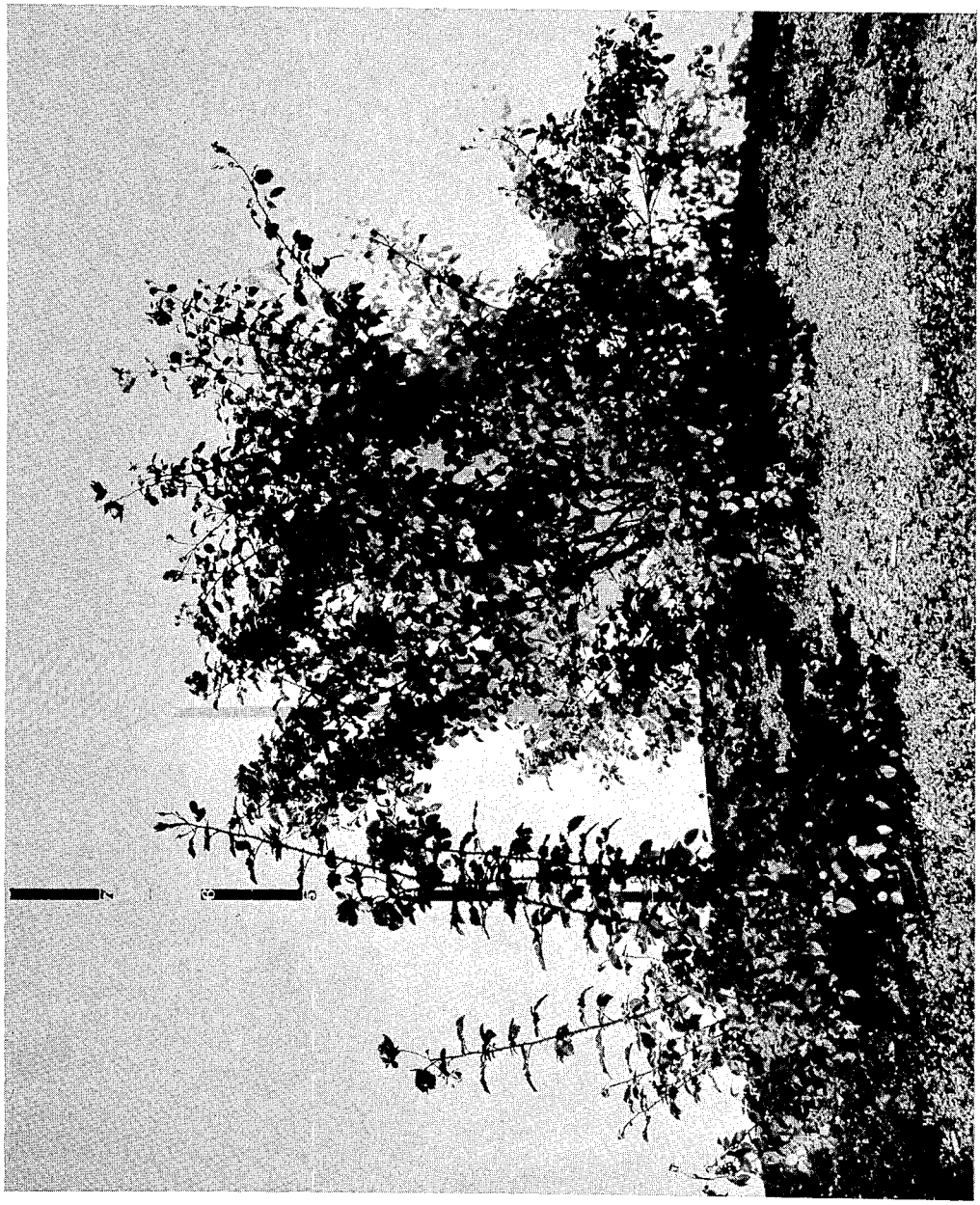
Inventors
D. L. Armstrong and
H. C. Swim
By: Robb & Robb
Attorneys.

United States Patent Office

Plant Pat. 2,488
Patented Mar. 16, 1965

2,488
ROSE PLANT

David L. Armstrong and Herbert C. Swim, both of Ontario, Calif., assignors to Armstrong Nurseries, Inc., Ontario, Calif., a corporation of California Filed Jan. 16, 1964, Ser. No. 338,272
1 Claim. (Cl. Plt.—2)

The present invention relates to a new and distinct variety of rose plant of the clambing floribunda class, which was originated by us by crossing the variety "Buccaneer" (Plant Patent No. 1,119) with the variety "Circus" (Plant Patent No. 1,382), the former being the seed parent, and the latter being the pollen parent.

This variety has been selected by us for its outstanding features which represent a new and improved combination resulting from an extensive breeding program having as its objective to produce improved new rose varieties of the multi-color type and yellow color range combined with various types of plant habit. These objectives have been substantially achieved in the new variety, along with other desirable improvements, as evidenced by the following characteristics which are outstanding in the new variety and which distinguish it from its parents, as well as from all other varieties of which we are aware:

(1) Ever blooming, bushy, free-standing, floribunda type, vigorous, upright-spreading climbing habit which can be left as a large bushy shrub or trained as a typical climbing plant, having short to long arching or climbing canes up to 5 or 6 feet in length on established plants, with all canes terminating in small to medium size flower clusters and usually producing much lateral growth varying from simple short flower clusters to new long canes also having flowers later in the same season, as well as some flowering from long canes the next season;

(2) Foliage of medium to large size which covers the plant well and is quite mildew resistant and attractive, resembling the foliage of the parent variety "Circus";

(3) Excellent bud form of urn shape;

(4) Outstanding floriferousness, similar to the parent variety "Circus," with semi-double flowers usually borne in clusters of from small to medium size; and (5) A distinctive and attractive flower color which changes with age and exposure to light in a strongly contrasting and attractive manner, from the rather bright yellow of the newly opening flower through warm blends of yellow and pink and red, to the mostly red color of the old flowers, with the yellow color lingering longest in the center of the flower.

In comparison with its seed parent, "Buccaneer," the new variety resembles this parent to some degree in its habit of growth, but is more spreading and bushy, and produces considerably longer canes and climbing canes than this parent; it produces its flowers in clusters of from small to medium size, whereas the flowers of this parent are borne either singly or in small clusters; the new variety is only semi-double in its flower petalage, whereas the petalage of this parent is considerably greater; and the flowers of this parent are yellow, whereas those of the new variety are multi-color yellow and red and colors therebetween.

As compared with its pollen parent, "Circus," the habit of the new variety is essentially that of a climber, whereas this parent has a strictly bush habit; the flowers of the new variety are only semi-double in petalage, instead of being more double like the flowers of this parent; and while both the new variety and this parent bear multicolor flowers of the same general type, the flowers of the new variety have much stronger and brighter colors, with more contrast between the yellow and red colors.

Asexual reproduction of our new variety by budding, as performed at Ontario, California, shows that the foregoing characteristics and distinctions come true to form and are established and transmitted through succeeding propagations.

The accompanying drawings show typical specimens of the vegetative growth and flowers of our new variety in different stages of development, with some of the flowers and vegetative growth being depicted in color as nearly true as it is reasonably possible to make the same in a color illustration of this character, and there being two typical established plants depicting in black and white the climbing habit of the new variety unpruned, with the smaller of these plants being one year old from the time of planting, and the larger being a two-year plant.

The following is a detailed description of the new variety, with color terminology in accordance with Robert F. Wilson's Horticultural Colour Chart (hereinafter abbreviated as (W)) and Robert Ridgway's Color Standards and Nomenclature (hereinafter abbreviated as (R)), as indicated:

Type: Pillar; climbing; outdoor; seeding; for cut flowers and for garden decoration.
Class: Climbing floribunda.
Breeding: Seedling.
*Seed parent.*—"Buccaneer."
*Pollen parent.*—"Circus."
Propagation: Holds its distingiushing characteristics through succeeding propagations by budding.

*Flower*

Locality where grown and observed: Ontario, California.
Flowers borne: Sometimes singly, but usually 5 or more to a stem; in irregular, usually flat clusters; on strong stems ranging from short to medium length.
Quantity of bloom: Abundant, outdoors.
Continuity: Nearly continuous during growing season.
Fragrance: Slight.
Bud:

*Peduncle.*—Average length; average caliper; erect; with few prickles and from several to many small stipitate glands. Color—near Apple Green, Plate XVII (R), with side exposed to sun near Courage Green, Plate XVII (R).

*Before calyx breaks.*—Size—from small to medium. Form—medium length; from pointed to ovoid.

*As calyx breaks.*—Color—between Cardinal Red, Plate 822/2, page 168 (W) and Chrysanthemum Crimson, Plate 824/1, page 169 (W) where longest exposed to light, with small areas or lines of near Lemon Yellow, Plate 4, page 4 (W) showing where sepal has just pulled away from petal.

*Sepals.*—Inner surface—with fine wooly tomentum. Outer surface—with several to many small stipitate glands. Alternate margins—lined with fine wooly tomentum. Other margins—with several to many small stipitate glands and small foliaceous appendages.

*As first petal opens.*—Size—from small to average. Form—medium length; from ovoid to urn-shaped. Color: outside—mostly between Currant Red, Plate 821/3, page 167 (W) and Cardinal Red, Plate 822, page 168 (W), with some near Lemon Yellow, Plate 4, page 4 (W), particularly at base of petal, with some intermediate blending from near Marigold Orange, Plate 11/2, page 11 (W) to Fire Red, Plate 15/2, page 15 (W); inside—near Marigold Orange, Plate 11/2, page 11 (W), washed lightly and sometimes marked with near Carmine, Plate 21, page 21 (W) toward margins, and blending into near Lemon Yellow, Plate 4, page 4 (W) toward base.

*Opening.*—Opens up well; is not retarded or prevented from opening by cold, hot, wet or dry weather.

Bloom:

*Size (when fully open).*—From small to average; from 2½ inches to 3 inches.

*Petalage.*—Semi-double; from 12 to 18 petals, plus 2 to 4 petaloids; arranged irregularly.

*Form.*—High-centered at first, but becoming flat when open; petals being at first loosely cupped, with tips rolled outward, but later becoming more loosely flat, with tips rolled outward at maturity.

Petals:

*Texture.*—Medium thickness; moderately leathery.

*Appearance.*—Inside—satiny. Outside—satiny.

*Shape.*—Outside—between round and broadly obovate, with apex flat and sometimes with 1 or 2 notches. Intermediate—broadly obovate, with apex from rounded to flat and sometimes with 1 or 2 notches. Inside—obovate, with apex rounded.

This description of a newly opened flower was made from a rose grown outdoors during the month of August in Ontario, California:

*Color.*—Outer petal; outside surface—near Mandarin Red, Plate 17/2, page 17 (W), with tinges of near Carmine, Plate 21/1, page 21 (W) toward outer margins and changing to near Lemon Yellow, Plate 4/2, page 4 (W) at base, with original outermost 2 or 3 petals being the same as described when first petal opens; inside surface—near Saturn Red, Plate 13/2, page 13 (W), washed toward margins with from near Geranium Lake, Plate 20/2, page 20 (W) to near Carmine, Plate 21/1, page 21 (W), and changing at base to near Lemon Yellow, Plate 4, page 4 (W). Inner petal: outside surface—near Apricot, Plate 609/2, page 70 (W), blending with near Empire Yellow, Plate 603, page 66 (W) toward base, with small area at base near Aureolin, Plate 3/1, page 3 (W); inside surface—between Lemon Yellow, Plate 4, page 4 (W) and Lemon Yellow, Plate 4/2, page 4 (W), becoming near Apricot, Plate 609/1, page 70 (W), with some shadings of near Geranium Lake, Plate 20/2, page 20 (W) toward margins.

This description was made from a rose that was open for three days outdoors during the month of August at Ontario, California:

*Color.*—Outer petal: outside surface—between near Crimson, Plate 22/3, page 22 (W) and near Rose Madder, Plate 23/2, page 23 (W), marked on the two or three original outside petals with near Cardinal Red, Plate 822/3, page 168 (W), blending toward base with near Empire Yellow, Plate 603/3, page 66 (W), and with small area at base near Empire Yellow, Plate 603, page 66 (W); inside surface—between Carmine, Plate 21/2, page 21 (W) and Crimson, Plate 22/1, page 22 (W), blending into between Empire Yellow, Plate 603/1, page 66 (W) and Empire Yellow, Plate 603, page 66 (W) toward base. Inner petal: outside surface—between Azalea Pink, Plate 618/1, page 74 (W) and Carmine Rose, Plate 621/1, page 75 (W) blending toward base into near Empire Yellow, Plate 603/1, page 66 (W); inside surface—between Geranium Lake, Plate 20/2, page 20 (W) and Carmine, Plate 21/2, page 21 (W), blending toward base into near Empire Yellow, Plate 603/1, page 66 (W).

*General color effect.*— Newly opened flower—near Apricot, Plate 609/1, page 70 (W), tinged near the edge of the flower with near Geranium Lake, Plate 20/2, page 20 (W) and blending at the center into near Lemon Yellow, Plate 4, page 4 (W). 3-days open—between Geranium Lake, Plate 20/2, page 20 (W) and Carmine, Plate 21/1, page 21 (W), with some near Empire Yellow, Plate 603/1, page 66 (W) at center. Longer than 3-days open—between Carmine, Plate 21/1, page 21 (W) and Currant Red, Plate 821/3, page 167 (W).

*Behavior.*—Drop off cleanly; not particularly affected by cold, hot, wet or dry weather.

*Flower longevity.*—On bush in garden—4 or 5 days in September. Cut roses grown outdoors and kept at living-room temperatures—4 or 5 days in September.

*Reproductive organs*

Stamens: Average number; arranged regularly about pistils; a few mixed with petaloids.

Filaments: From short to medium length (from 3 mm. to 10 mm. long); most with anthers. Color—near Lemon Yellow, Plate 4, page 4 (W).

Anthers: Small size; all open approximately at once. Color: upper side—margins near Cadmium Orange, Plate 8/1, page 8 (W), with remainder near Straw Yellow, Plate 604/1, page 67 (W); underside—margins near Cadmium Orange, Plate 8/1, page 8 (W), with remainder near Straw Yellow, Plate 604/1, page 67 (W).

Pollen: Abundant. Color—near Tangerine Orange, Plate 9, page 9 (W).

Pistils: Average number (from approximately 35 to 40).

Styles: Moderately even; short (from 3 mm. to 8 mm. long); thin; bunched. Color—base of style near Uranium Green, Plate 63/2, page 63 (W), blending with near Geranium Lake, Plate 20/2, page 20 (W) toward stigma.

Stigma: Color—near Chinese Yellow, Plate 606/1, page page 68 (W).

Ovaries: Usually all enclosed in calyx.

Hips: From short to average length; globular; smooth; walls thick and fleshy. Color—near Orange, Plate 12/1, page 12 (W).

Sepals: Falling soon; medium length; usually straight. Color: inside—near Light Grape Green, Plate XLI (R); outside—near Absinthe Green, Plate XXXI (R).

Seeds: From few to many (from 4 to 10); from small to medium size.

*Plant*

Foliage:

*Leaves.*—Compound of usually 3–7 leaflets; abundant; from medium size to large; somewhat leathery; semi-glossy.

*Leaflets.*—Shape—between oval and ovate, with apex acute. Base—round. Margin—doubly serrate.

*Color.*—Mature: upper surface—near Cress Green, Plate XXXI (R); under surface—near Light Elm Green, Plate XVII (R). Young: upper surface—near Bice Green, Plate XVII (R); under surface—near Chromium Green, plate XXXII (R).

*Rachis (the supporting stem of the compound leaf).*—From average size to heavy. Upper side—grooved; with from few to many small stipitate glands on edges. Under side—moderately smooth; with from few to many small stipitate glands and from few to several prickles of small to medium size.

*Stipules.*—From short to medium length; narrow; with points of from short to medium length turning out at an angle of more than 45°.

*Disease resistance.*—Better than average resistance to mildew as compared with other varieties grown under comparable cultural conditions at Ontario, California.

Growth:

*Habit.*—Upright-spreading; climbing; much branched.

*Growth.*—Vigorous.

*Canes.*—Medium caliper.

*Main stems.*—Color—near Yellowish Oil Green, Plate V (R). Large prickles—from few to several; medium length; hooked downward; with narrow base of medium length; color—between Tawny Olive, Plate XXIX (R) and Snuff Brown, Plate XXIX (R). Small prickles—few; color—between Tawny Olive, Plate XXIX (R) and Snuff Brown, plate XXIX (R). Hairs—none.

*Branches.*—Color—near Rainette Green, Plate XXXI (R). Large prickles—several; from medium length to long; hooked slightly downward; with narrow base of medium length; color—between Tawny, Plate XV (R) and Cinnamon Brown, Plate XV (R). Small prickles—from none to very few; color—between Tawny, Plate XV (R) and Cinnamon Brown, Plate XV (R). Hairs—none.

*New Shoots.*—Color—near Scheele's Green, Plate VI (R). Large prickles—from several to many; from short to medium length; hooked slightly downward; with narrow base of medium length; color—near Calliste Green, Plate VI (R). Small prickles—from several to many; color—near Calliste Green, Plate VI (R). Hairs—none.

We claim:

A new and distinct variety of rose plant of the climbing floribunda, substantially as herein shown and described, characterized particularly as to novelty by the unique combination of ever blooming, bushy, free standing, vigorous, upright-spreading habit of growth, with from short to long arching or climbing canes suitable for use as a large and bushy shrub or for training as a typical climbing plant, with all growth terminating in clusters of flowers ranging from small to medium size and usually producing much lateral growth varying from simple short flower clusters to new long canes also having flowers later the same season, and with some flowering from long canes arising the next season, attractive and quite mildew resistant foliage ranging from medium to large size and covering the plant well, excellent bud form of urn shape, outstanding floriferousness, with semi-double flowers usually borne in clusters, but sometimes singly, and a distinctive flower color which changes with age and exposure to light in a strongly contrasting and attractive manner, ranging from a rather bright yellow in the newly opening flower through warm blends of yellow and pink and red colors to a mostly red color in the older flowers, with the yellow color lingering longest in the center of the flower.

No references cited.

ABRAHAM G. STONE, *Primary Examiner.*